US012622390B2

(12) United States Patent (10) Patent No.: US 12,622,390 B2
Bergemann et al. (45) Date of Patent: *May 12, 2026

(54) PLANTS AND SEEDS OF CORN VARIETY CV962284

(71) Applicant: Monsanto Technology LLC, St. Louis, MO (US)

(72) Inventors: Scott A. Bergemann, Northfield, MN (US); Mark J. Brinkman, Omaha, NE (US); Todd E. Frank, Olivia, MN (US); Zachary King, Northfield, MN (US); Wade E. Odland, St. Charles, MO (US); Nathaniel J. Page, Madison, WI (US)

(73) Assignee: Monsanto Technology LLC, St. Louis, MO (US)

( * ) Notice: Subject to any disclaimer, the term of this patent is extended or adjusted under 35 U.S.C. 154(b) by 195 days.

This patent is subject to a terminal disclaimer.

(21) Appl. No.: 18/397,432

(22) Filed: Dec. 27, 2023

(65) Prior Publication Data

US 2025/0212798 A1 Jul. 3, 2025

(51) Int. Cl.
*A01H 6/46* (2018.01)
*A01H 5/10* (2018.01)

(52) U.S. Cl.
CPC ............. *A01H 6/4684* (2018.05); *A01H 5/10* (2013.01)

(58) Field of Classification Search
None
See application file for complete search history.

(56) References Cited

U.S. PATENT DOCUMENTS

| | | | |
|---|---|---|---|
| 4,658,085 A | 4/1987 | Beversdorf et al. | |
| 5,523,520 A | 6/1996 | Hunsperger et al. | |
| 5,773,683 A | 6/1998 | Foley | |
| 6,433,261 B2 | 8/2002 | Hotchkiss | |
| 6,693,232 B1 | 2/2004 | Bergemann | |
| 6,852,915 B2 | 2/2005 | Johnson | |
| 10,194,607 B2 | 2/2019 | Nelson | |
| 10,499,580 B1 | 12/2019 | Turnbull | |
| 11,388,873 B2 * | 7/2022 | Maxwell | A01H 5/10 |
| 2025/0212799 A1 * | 7/2025 | Adhikari | A01H 5/10 |
| 2025/0212800 A1 * | 7/2025 | Adhikari | A01H 5/10 |
| 2025/0212802 A1 * | 7/2025 | Bergemann | A01H 5/10 |
| 2025/0212804 A1 * | 7/2025 | Adhikari | A01H 6/4684 |
| 2025/0212805 A1 * | 7/2025 | Adhikari | A01H 5/10 |
| 2025/0212806 A1 * | 7/2025 | Adhikari | A01H 6/4684 |

OTHER PUBLICATIONS

Plant and Soil Sciences eLibrary: Advanced backcross breeding (2023); downloaded on Aug. 26, 2023; pp. 1-3 (Year: 2023).*
Moore, M. A shallow gene pool (2008) Farm Industry News; pp. 1-3 (Year: 2008).*
Crossa et al., "Genomic Selection in Plant Breeding: Methods, Models, and Prespectives", Trends in Plant Science, 22(11): pp. 961-975, 2017.
Eshed et al., "Less-Than-Addictive Epistatic Interactions of Quantitative Trait Loci in Tomato," Genetics, 143:1807-1817, 1996.
Fehr (ed), "Backcross Method," In: Principles of Cultivar Development, vol. 1: Theory and Technique, pp. 360-376, 1987.
Gaj et al., "ZFN, TALEN and CRISPR/Cas-Based Methods for Genome Engineering," Trends Biotechnol, 31(7): 397-405, 2013.
Hallauer et al., "Corn Breeding," In: Corn and Corn Improvement, Sprague et al. (Eds.), Madison, Wisconsin, Ch. 8, pp. 463-564, 1988.
Khandagale et al., "Genome Editing for Targeted Improvement of Plants," Plant Biotechnol Rep, 10:327-343, 2016.
Kraft et al.,"Linkage Disequilibrium and Fingerprinting in Sugar Beet," Theor Appl Genet, 101:323-326, 2000.
Krakowsky et al., "Quantitative, Trait loci for Cell Wall Components in Recombinant Inbred Lines of Maize (*Zea mays* L.) II: Leaf sheath Tissue," Theor Appl Genet 112:717-726, 2006.
Larson et al., "Corn Production," In: Corn and Corn Improvement, G.F. Sprague (Ed.), No. 18 in Agronomy Series, American Society Agronomy, Inc., Madison, Wisconsin, pp. 625-669, 1977.
Meghji et al., "Inbreeding Depression, Inbred and Hybrid Grain Yields, and Other Traits of Maize Genotypes Representing Three Eras," Crop Science, 24:545-549, 1984.
Openshaw et al., "Marker-assisted Selection in Backcross Breeding," In: Proceedings Symposium of the Analysis of Molecular Data, Crop Science Society of America pp. 41-43, 1994.
Sprague et al., "Corn Breeding," In: Corn and Corn Improvement, G.F. Sprague (Ed.), No. 18 in Agronomy Series, American Society Agronomy, Inc., Madison, Wisconsin, pp. 305-362, 1977.
Wych, Production of Hybrid Seed Corn, In: Corn and Corn Improvement, Sprague et al. (Eds.), Madison, Wisconsin, Ch. 9, pp. 565-607, 1988.
Variety specific information as indicated in Transmittal Letter for U.S. Appl. No. 18/397,432 dated Aug. 12, 2025.
Adhikari et al., U.S. Appl. No. 18/932,336, filed Oct. 30, 2024.
Adhikari et al., U.S. Appl. No. 18/941,417, filed Nov. 8, 2024.

* cited by examiner

*Primary Examiner* — Cathy Kingdon
(74) *Attorney, Agent, or Firm* — Paul D. Tietz; Ann H. Inglett; Gale Wesley Starkey

(57) ABSTRACT

According to the disclosure, there is provided seed and plants of the corn variety designated CV962284. The disclosure thus relates to the plants, seeds, and tissue cultures of the variety CV962284, and to methods for producing a corn plant produced by crossing a corn plant of variety CV962284 with itself or with another corn plant, such as a plant of another variety. The disclosure further relates to corn seeds and plants produced by crossing plants of variety CV962284 with plants of another variety, such as another inbred line. The disclosure further relates to the inbred and hybrid genetic complements of plants of variety CV962284.

20 Claims, No Drawings

PLANTS AND SEEDS OF CORN VARIETY CV962284

BACKGROUND

Field

The present disclosure relates to the field of corn breeding. In particular, the disclosure relates to corn seed and plants of the variety designated CV962284, and derivatives and tissue cultures thereof.

Description

The goal of field crop breeding is to combine various desirable traits in a single variety/hybrid. Such desirable traits include greater yield, better stalks, better roots, resistance to insecticides, herbicides, pests, and disease, tolerance to heat and drought, reduced time to crop maturity, better agronomic quality, higher nutritional value, and uniformity in germination times, stand establishment, growth rate, maturity, and fruit size.

Breeding techniques take advantage of a plant's method of pollination. There are two general methods of pollination: a plant self-pollinates if pollen from one flower is transferred to the same or another flower of the same plant. A plant cross-pollinates if pollen comes to it from a flower on a different plant.

Corn plants (*Zea mays* L.) can be bred by both self-pollination and cross-pollination. Both types of pollination involve the corn plant's flowers. Corn has separate male and female flowers on the same plant, located on the tassel and the ear, respectively. Natural pollination occurs in corn when wind blows pollen from the tassels to the silks that protrude from the tops of the ear shoot.

Plants that have been self-pollinated and selected for type over many generations become homozygous at almost all gene loci and produce a uniform population of true breeding progeny, a homozygous plant. A cross between two such homozygous plants produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform corn plant hybrids requires the development of homozygous inbred plants, the crossing of these inbred plants, and the evaluation of the crosses. Pedigree breeding and recurrent selection are examples of breeding methods used to develop inbred plants from breeding populations. Those breeding methods combine the genetic backgrounds from two or more inbred plants or various other broad-based sources into breeding pools from which new inbred plants are developed by selfing and selection of desired phenotypes. The new inbreds are crossed with other inbred plants and the hybrids from these crosses are evaluated to determine which of those have commercial potential.

North American farmers plant tens of millions of acres of corn and there are extensive national and international commercial corn breeding programs. A continuing goal of these corn breeding programs is to develop corn hybrids that are based on stable inbred plants and have one or more desirable characteristics. To accomplish this goal, the corn breeder must select and develop superior inbred parental plants.

SUMMARY

The present disclosure provides a corn plant of the variety designated CV962284. Also provided are corn plants having all the morphological and physiological characteristics of the inbred corn variety CV962284. The inbred corn plant may further comprise, or have, a cytoplasmic or nuclear factor that may confer male sterility or otherwise preventing self-pollination, such as by self-incompatibility. Parts of the corn plant of the present disclosure are also provided, for example, pollen obtained from an inbred plant and an ovule of the inbred plant.

The disclosure also concerns seed of the inbred corn variety CV962284. The inbred corn seed may be provided as an essentially homogeneous population of inbred corn seed of the variety designated CV962284. Essentially homogeneous populations of inbred seed are generally free from substantial numbers of other seed. Therefore, in the practice of the present disclosure, inbred seed forms at least about 97% of the total seed. The population of inbred corn seed may be particularly defined as being essentially free from hybrid seed. The inbred seed population may be separately grown to provide an essentially homogeneous population of inbred corn plants designated CV962284.

In a further aspect, a composition is provided comprising a seed of corn variety CV962284 comprised in plant seed growth media. In certain embodiments, the plant seed growth media is a soil or synthetic cultivation medium. In specific embodiments, the growth medium may be comprised in a container or may, for example, be soil in a field.

In another aspect, a plant of corn variety CV962284 comprising an added heritable trait is provided. The heritable trait may comprise a genetic locus that is a dominant or recessive allele. In one embodiment, a plant of corn variety CV962284 further comprising a single locus conversion is provided. In specific embodiments, an added genetic locus confers one or more traits such as, for example, male sterility, herbicide tolerance, insect resistance, disease resistance, waxy starch, modified fatty acid metabolism, modified phytic acid metabolism, modified carbohydrate metabolism and modified protein metabolism. In certain embodiments, a trait that confers herbicide resistance may confer resistance to herbicides such as, for example, imidazolinone herbicides, sulfonylurea herbicides, triazine herbicides, phenoxy herbicides, cyclohexanedione herbicides, benzonitrile herbicides, 4-hydroxyphenylpyruvate dioxygenase-inhibiting herbicides, protoporphyrinogen oxidase-inhibiting herbicides, acetolactate synthase-inhibiting herbicides, 1-aminocyclopropane-1-carboxylic acid synthase-inhibiting herbicides, bromoxynil, nicosulfuron, 2,4-dichlorophenoxyacetic acid (2,4-D), dicamba, quizalofop-p-ethyl, glyphosate, or glufosinate. In certain embodiments, an insect inhibitory composition may comprise one of The PirA Proteins, The PirB Proteins, or The PirAB Fusion Proteins, or a related protein can further comprise at least one additional polypeptide known to those of ordinary skill in the art that exhibits insect inhibitory activity against the same Lepidopteran, Coleopteran, or Hemipteran insect species, but which is different from The PirA Proteins, The PirB Proteins, or The PirAB Fusion Proteins, or a related toxin protein. Possible additional polypeptides for such a composition include an insect inhibitory protein and an insect inhibitory dsRNA molecule. A conferred trait may be, for example, conferred by a naturally occurring maize gene introduced into the genome of the variety by backcrossing, a natural or induced mutation, or a transgene introduced through genetic transformation techniques. When introduced through transformation, a genetic locus may comprise one or more transgenes integrated at a single chromosomal location.

In further embodiments, a single locus conversion comprises a genetic modification to the genome of corn variety CV962284. A genetic modification may comprise, for example, an insertion, deletion, or substitution of a nucleotide sequence. In certain embodiments, a single locus may comprise one or more genes or intergenic regions integrated into or mutated at a single locus or may comprise one or more nucleic acid molecules integrated at the single locus. In particular embodiments, a single locus conversion may be generated by genome editing such as through use of engineered nucleases, as is known in the art. Examples of engineered nucleases include, but are not limited to, Cas endonucleases, zinc finger nucleases (ZFNs), transcription activator-like effector nucleases (TALENs), and engineered meganucleases, also known as homing endonucleases. Naturally occurring nucleases can also find use for genome editing. In specific embodiments, endonucleases, both naturally occurring and engineered, may utilize any polypeptide-, DNA-, or RNA-guided genome editing systems known to the skilled artisan.

In yet another aspect, an inbred corn plant of the variety designated CV962284 is provided, wherein a cytoplasmically-inherited trait has been introduced into said inbred plant. Such cytoplasmically inherited traits are passed to progeny through the female parent in a particular cross. An exemplary cytoplasmically-inherited trait is the male sterility trait. Cytoplasmic-male sterility (CMS) is a pollen abortion phenomenon determined by the interaction between the genes in the cytoplasm and the nucleus. Alteration in the mitochondrial genome and the lack of restorer genes in the nucleus will lead to pollen abortion. With either a normal cytoplasm or the presence of restorer gene(s) in the nucleus, the plant will produce pollen normally. A CMS plant can be pollinated by a maintainer version of the same variety, which has a normal cytoplasm but lacks the restorer gene(s) in the nucleus and continue to be male sterile in the next generation. The male fertility of a CMS plant can be restored by a restorer version of the same variety, which must have the restorer gene(s) in the nucleus. With the restorer gene(s) in the nucleus, the offspring of the male-sterile plant can produce normal pollen grains and propagate. A cytoplasmically inherited trait may be a naturally occurring maize trait or a trait introduced through genetic transformation techniques.

In yet another aspect, a tissue culture of regenerable cells of a plant of variety CV962284 is provided. The tissue culture will preferably be capable of regenerating plants capable of expressing all the morphological and physiological characteristics of the variety, and of regenerating plants having substantially the same genotype as other plants of the variety. Examples of some of the morphological and physiological characteristics that may be assessed include characteristics related to yield, maturity, and kernel quality. The regenerable cells in such tissue cultures will preferably be derived from embryos, meristematic cells, immature tassels, microspores, pollen, leaves, anthers, roots, root tips, silk, flowers, kernels, ears, cobs, husks, or stalks, or from callus or protoplasts derived from those tissues. Still further, the present disclosure provides corn plants regenerated from the tissue cultures, the plants having all the morphological and physiological characteristics of variety CV962284.

In yet another aspect, processes are provided for producing corn seeds or plants, which comprise crossing a first parent corn plant as a male or female parent with a second parent corn plant, wherein at least one of the first or second parent corn plants is a plant of the variety designated CV962284. These processes may be further exemplified as processes for preparing hybrid corn seed or plants, wherein a first inbred corn plant is crossed with a second corn plant of a different, distinct variety to provide a hybrid that has, as one of its parents, the inbred corn plant variety CV962284. In these processes, crossing will result in the production of seed. The seed production occurs regardless of whether the seed is collected or not.

In one embodiment, the first step in "crossing" comprises planting, preferably in pollinating proximity, seeds of a first and second parent corn plant, and preferably, seeds of a first inbred corn plant and a second, distinct inbred corn plant. Where the plants are not in pollinating proximity, pollination can nevertheless be accomplished by transferring a pollen or tassel bag from one plant to the other as described below.

A second step comprises cultivating or growing the seeds of said first and second parent corn plants into plants that bear flowers (corn bears both male flowers (tassels) and female flowers (silks) in separate anatomical structures on the same plant). A third step comprises preventing self-pollination of the plants, i.e., preventing the silks of a plant from being fertilized by any plant of the same variety, including the same plant. This is preferably done by emasculating the male flowers of the first or second parent corn plant, (i.e., treating or manipulating the flowers to prevent pollen production, to produce an emasculated parent corn plant). Self-incompatibility systems may also be used in some hybrid crops for the same purpose. Self-incompatible plants still shed viable pollen and can pollinate plants of other varieties but are incapable of pollinating themselves or other plants of the same variety.

A fourth step may comprise allowing cross-pollination to occur between the first and second parent corn plants. When the plants are not in pollinating proximity, this is done by placing a bag, usually paper or glassine, over the tassels of the first plant and another bag over the silks of the incipient ear on the second plant. The bags are left in place for at least 24 hours. Since pollen is viable for less than 24 hours, this assures that the silks are not pollinated from other pollen sources, that any stray pollen on the tassels of the first plant is dead, and that the only pollen transferred comes from the first plant. The pollen bag over the tassel of the first plant is then shaken vigorously to enhance release of pollen from the tassels, and the shoot bag is removed from the silks of the incipient ear on the second plant. Finally, the pollen bag is removed from the tassel of the first plant and is placed over the silks of the incipient ear of the second plant, shaken again and left in place. Yet another step comprises harvesting the seeds from at least one of the parent corn plants. The harvested seed can be grown to produce a corn plant or hybrid corn plant.

Disclosed herein are corn seed and plants produced by a process that comprises crossing a first parent corn plant with a second parent corn plant, wherein at least one of the first or second parent corn plants is a plant of the variety designated CV962284. In one embodiment, corn seed and plants produced by the process are first generation ($F_1$) hybrid corn seed and plants produced by crossing an inbred with another, distinct inbred. This disclosure further contemplates seed of an $F_1$ hybrid corn plant. Therefore, certain exemplary embodiments provide an $F_1$ hybrid corn plant and seed thereof.

In still yet another aspect, the genetic complement of the corn plant variety designated CV962284 is provided. The phrase "genetic complement" is used to refer to the aggregate of nucleotide sequences, the expression of which sequences defines the phenotype of, in the present case, a corn plant, or a cell or tissue of that plant. A genetic complement thus represents the genetic makeup of an inbred cell, tissue or plant, and a hybrid genetic complement represents the genetic makeup of a hybrid cell, tissue, or plant. The disclosure thus provides corn plant cells that have a genetic complement in accordance with the inbred corn plant cells disclosed herein, and plants, seeds and diploid plants containing such cells.

Plant genetic complements may be assessed by genetic marker profiles, and by the expression of phenotypic traits that are characteristic of the expression of the genetic complement, e.g., isozyme typing profiles. It is understood that variety CV962284 could be identified by any of the many well-known techniques.

In still yet another aspect, the present disclosure provides hybrid genetic complements, as represented by corn plant cells, tissues, plants, and seeds, formed by the combination of a haploid genetic complement of a corn plant with a haploid genetic complement of the same or a different variety. In another aspect, the present disclosure provides a corn plant regenerated from a tissue culture that comprises a hybrid genetic complement of this disclosure.

In still yet another aspect, the present disclosure provides a method of producing an inbred corn plant derived from the corn variety CV962284, the method comprising the steps of: (a) preparing a progeny plant derived from corn variety CV962284, wherein said preparing comprises crossing a plant of the corn variety CV962284 with a second corn plant; (b) crossing the progeny plant with itself or a second plant to produce a seed of a progeny plant of a subsequent generation; (c) growing a progeny plant of a subsequent generation from said seed of a progeny plant of a subsequent generation and crossing the progeny plant of a subsequent generation with itself or a second plant; and (d) repeating the steps for an additional 3-10 generations to produce an inbred corn plant derived from the corn variety CV962284. In the method, it may be desirable to select plants resulting from step (c) for continued crossing according to steps (b) and (c). By selecting plants having one or more desirable traits, an inbred corn plant derived from the corn variety CV962284 is obtained that possesses some of the desirable traits of corn variety CV962284 as well as potentially other selected traits.

DETAILED DESCRIPTION

Definitions of Plant Characteristics

Barren Plants: Plants that are barren, i.e., lack an ear with grain, or have an ear with only a few scattered kernels.

Cg: *Colletotrichum graminicola* rating. The rating multiplied by 10 is approximately equal to percent total plant infection.

CLN: Corn Lethal Necrosis (combination of Maize Chlorotic Mottle Virus and Maize Dwarf Mosaic virus) rating. A numerical rating that is based on a 1 to 9 scale of severity in which "1" indicates "most resistant" and "9" indicates "most susceptible."

Cn: *Corynebacterium nebraskense* rating. The rating multiplied by 10 is approximately equal to percent total plant infection.

Cz: *Cercospora zeae-maydis* rating. The rating multiplied by 10 is approximately equal to percent total plant infection.

Dgg: *Diatraea grandiosella* girdling rating. A rating in which the value equals percent plants girdled, and stalk lodged.

Dropped Ears: Ears that have fallen from the plant to the ground.

Dsp: *Diabrotica* species root rating. A rating that is based on a 1 to 9 scale in which "1" indicates "least affected" and "9" indicates "severe pruning."

Ear-Attitude: The attitude or position of the ear at harvest, which is scored as upright, horizontal, or pendant.

Ear-Cob Color: The color of the cob, which is scored as white, pink, red, or brown.

Ear-Cob Diameter: The average diameter of the cob when measured at the midpoint.

Ear-Cob Strength: A measure of mechanical strength of the cobs to breakage, which is scored as strong or weak.

Ear-Diameter: The average diameter of the ear when measured at the midpoint.

Ear-Dry Husk Color: The color of the husks at harvest, which is scored as buff, red, or purple.

Ear-Fresh Husk Color: The color of the husks 1 to 2 weeks after pollination, which is scored as green, red, or purple.

Ear-Husk Bract: The length of an average husk leaf, which is scored as short, medium, or long.

Ear-Husk Cover: The average distance from the tip of the ear to the tip of the husks in which the minimum value is no less than zero.

Ear-Husk Opening: An evaluation of husk tightness at harvest, which is scored as tight, intermediate, or open.

Ear-Length: The average length of the ear.

Ear-Number Per Stalk: The average number of ears per plant.

Ear-Shank Internodes: The average number of internodes on the ear shank.

Ear-Shank Length: The average length of the ear shank.

Ear-Shelling Percent: The average of the shelled grain weight divided by the sum of the shelled grain weight and cob weight for a single ear.

Ear-Silk Color: The color of the silk observed 2 to 3 days after silk emergence, which is scored as green-yellow, yellow, pink, red, or purple.

Ear-Taper (Shape): The taper or shape of the ear, which is scored as conical, semi-conical, or cylindrical.

Ear-Weight: The average weight of an ear.

Early Stand: The percent of plants that emerge from the ground as determined in the early spring.

ER: Ear rot rating. A rating in which the value approximates percent ear rotted.

Final Stand Count: The number of plants just prior to harvest.

GDUs: Growing degree units. GDUs are calculated by the Barger Method in which the heat units for a 24 h period are calculated as follows: [(Maximum daily temperature+Minimum daily temperature)/2]−50. The highest maximum daily temperature used is 86° F. and the lowest minimum temperature used is 50° F.

GDUs to Shed: The number of growing degree units (GDUs) or heat units required for an inbred line or hybrid to have approximately 50% of the plants shedding pollen as measured from time of planting. GDUs to shed is determined by summing the individual GDU daily values from the planting date to the date of 50% pollen shed.

GDUs to Silk: The number of growing degree units (GDUs) for an inbred line or hybrid to have approximately 50% of the plants with silk emergence as measured from the time of planting. GDUs to silk is determined by summing the individual GDU daily values from the planting date to the date of 50% silking.

Hc2: *Helminthosporium carbonum* race 2 rating. The rating multiplied by 10 is approximately equal to percent total plant infection.

Hc3: *Helminthosporium carbonum* race 3 rating. The rating multiplied by 10 is approximately equal to percent total plant infection.

Hm: *Helminthosporium maydis* race 0 rating. The rating multiplied by 10 is approximately equal to percent total plant infection.

Ht1: *Helminthosporium turcicum* race 1 rating. The rating multiplied by 10 is approximately equal to percent total plant infection.

Ht2: *Helminthosporium turcicum* race 2 rating. The rating multiplied by 10 is approximately equal to percent total plant infection.

HtG: Chlorotic-lesion type resistance. "+" indicates the presence of Ht chlorotic-lesion type resistance; "–" indicates absence of Ht chlorotic-lesion type resistance; and "+/–" indicates segregation of Ht chlorotic-lesion type resistance. The rating multiplied by 10 is approximately equal to percent total plant infection.

Kernel-Aleurone Color: The color of the aleurone, which is scored as white, pink, tan, brown, bronze, red, purple, pale purple, colorless, or variegated.

Kernel-Cap Color: The color of the kernel cap observed at dry stage, which is scored as white, lemon-yellow, yellow, or orange.

Kernel-Endosperm Color: The color of the endosperm, which is scored as white, pale yellow, or yellow.

Kernel-Endosperm Type: The type of endosperm, which is scored as normal, waxy, or opaque.

Kernel-Grade: The percent of kernels that are classified as rounds.

Kernel-Length: The average distance from the cap of the kernel to the pedicel.

Kernel-Number Per Row: The average number of kernels in a single row.

Kernel-Pericarp Color: The color of the pericarp, which is scored as colorless, red-white crown, tan, bronze, brown, light red, cherry red, or variegated.

Kernel-Row Direction: The direction of the kernel rows on the ear, which is scored as straight, slightly curved, spiral, or indistinct (scattered).

Kernel-Row Number: The average number of rows of kernels on a single ear.

Kernel-Side Color: The color of the kernel side observed at the dry stage, which is scored as white, pale yellow, yellow, orange, red, or brown.

Kernel-Thickness: The distance across the narrow side of the kernel.

Kernel-Type: The type of kernel, which is scored as dent, flint, or intermediate.

Kernel-Weight: The average weight of a predetermined number of kernels.

Kernel-Width: The distance across the flat side of the kernel.

Kz: *Kabatiella zeae* rating. The rating multiplied by 10 is approximately equal to percent total plant infection.

Leaf-Angle: Angle of the upper leaves to the stalk, which is scored as upright (0 to 30 degrees), intermediate (30 to 60 degrees), or lax (60 to 90 degrees).

Leaf-Color: The color of the leaves 1 to 2 weeks after pollination, which is scored as light green, medium green, dark green, or very dark green.

Leaf-Length: The average length of the primary ear leaf.

Leaf-Longitudinal Creases: A rating of the number of longitudinal creases on the leaf surface 1 to 2 weeks after pollination. Creases are scored as absent, few, or many.

Leaf-Marginal Waves: A rating of the waviness of the leaf margin 1 to 2 weeks after pollination, which is rated as none, few, or many.

Leaf-Number: The average number of leaves of a mature plant. Counting begins with the cotyledonary leaf and ends with the flag leaf.

Leaf-Sheath Anthocyanin: A rating of the level of anthocyanin in the leaf sheath 1 to 2 weeks after pollination, which is scored as absent, basal-weak, basal-strong, weak, or strong.

Leaf-Sheath Pubescence: A rating of the pubescence of the leaf sheath. Ratings are taken 1 to 2 weeks after pollination and scored as light, medium, or heavy.

Leaf-Width: The average width of the primary ear leaf when measured at its widest point.

LSS: Late season standability. The value multiplied by 10 is approximately equal to percent plants lodged in disease evaluation plots.

Moisture: The moisture of the grain at harvest.

On1: *Ostrinia nubilalis* 1st brood rating. The rating is based on a 1 to 9 scale in which "1" indicates "resistant" and "9" indicates "susceptible."

On2: *Ostrinia nubilalis* 2nd brood rating. The rating is based on a 1 to 9 scale in which "1" indicates "resistant" and "9" indicates "susceptible."

Relative Maturity: A maturity rating based on regression analysis. The regression analysis is developed by utilizing check hybrids and their previously established day rating versus actual harvest moistures. Harvest moisture on the hybrid in question is determined and that moisture value is inserted into the regression equation to yield a relative maturity.

Root Lodging: Root lodging is the percentage of plants that root lodge. A plant is counted as root lodged if a portion of the plant leans from the vertical axis by approximately 30 degrees or more.

Seedling Color: Color of leaves at the 6 to 8 leaf stage.

Seedling Height: Plant height at the 6 to 8 leaf stage.

Seedling Vigor: A visual rating of the amount of vegetative growth on a 1 to 9 scale in which the best and worst ratings are "1" and "9", respectively. The score is taken when the average entry in a trial is at the fifth leaf stage.

Selection Index: The selection index gives a single measure of hybrid's worth based on information from multiple traits. One of the traits that is almost always included is yield. Traits may be weighted according to the level of importance assigned to them.

Sr: *Sphacelotheca reiliana* rating. The rating is actual percent infection.

Stalk-Anthocyanin: A rating of the amount of anthocyanin pigmentation in the stalk. The stalk is rated 1 to 2 weeks after pollination as absent, basal-weak, basal-strong, weak, or strong.

Stalk-Brace Root Color: The color of the brace roots observed 1 to 2 weeks after pollination as green, red, or purple.

Stalk-Diameter: The average diameter of the lowest visible internode of the stalk.

Stalk-Ear Height: The average height of the ear when measured from the ground to the point of attachment of the ear shank of the top developed ear to the stalk.

Stalk-Internode Direction: The direction of the stalk internode observed after pollination as straight or zigzag.

Stalk-Internode Length: The average length of the internode above the primary ear.

Stalk Lodging: The percentage of plants that did stalk lodge. Plants are counted as stalk lodged if the plant is broken over or off below the ear.

Stalk-Nodes with Brace Roots: The average number of nodes having brace roots per plant.

Stalk-Plant Height: The average height of the plant when measured from the soil to the tip of the tassel.

Stalk-Tillers: The percent of plants that have tillers. A tiller is defined as a secondary shoot that has developed as a tassel capable of shedding pollen.

Staygreen: Staygreen is a measure of general plant health near the time of black layer formation (physiological maturity) and is usually recorded at the time the ear husks of most entries within a trial have turned a mature color. Scoring is on a 1 to 9 basis in which "1" and "9" are the best and worst score, respectively.

STR: Stalk rot rating. The rating is based on a 1 to 9 scale of severity in which "1" indicates "25% of inoculated internode rotted" and "9" indicates "entire stalk rotted and collapsed."

SVC: Southeastern Virus Complex (combination of Maize Chlorotic Dwarf Virus and Maize Dwarf Mosaic Virus) rating. The numerical rating is based on a 1 to 9 scale of severity in which "1" indicates "most resistant" and "9" indicates "most susceptible."

Tassel-Anther Color: The color of the anthers at 50% pollen shed, which is scored as green-yellow, yellow, pink, red, or purple.

Tassel-Attitude: The attitude of the tassel after pollination, which is scored as open or compact.

Tassel-Branch Angle: The angle of an average tassel branch to the main stem of the tassel, which is scored as upright (less than 30 degrees), intermediate (30 to 45 degrees), or lax (greater than 45 degrees).

Tassel-Branch Number: The average number of primary tassel branches.

Tassel-Glume Band: The closed anthocyanin band at the base of the glume, which is scored as present or absent.

Tassel-Glume Color: The color of the glumes at 50% shed, which is scored as green, red, or purple.

Tassel-Length: The length of the tassel, which is measured from the base of the bottom tassel branch to the tassel tip.

Tassel-Peduncle Length: The average length of the tassel peduncle, which is measured from the base of the flag leaf to the base of the bottom tassel branch.

Tassel-Pollen Shed: A visual rating of pollen shed that is determined by tapping the tassel and observing the pollen flow of approximately five plants per entry. The rating is based on a 1 to 9 scale in which "9" indicates "sterile" and "1" indicates "most pollen."

Tassel-Spike Length: The length of the spike, which is measured from the base of the top tassel branch to the tassel tip.

Test Weight: Weight of the grain in pounds for a given volume (bushel) adjusted to 15.5% moisture.

Yield: Yield of grain at harvest adjusted to 15.5% moisture.

Other Definitions

Allele: Any of one or more alternative forms of a gene locus, all which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny back to one of the parents, for example, a first-generation hybrid ($F_1$) with one of the parental genotypes of the $F_1$ hybrid.

Crossing: The pollination of a female flower of a corn plant, thereby resulting in the production of seed from the flower.

Cross-pollination: Fertilization by the union of two gametes from different plants.

Diploid: A cell or organism having two sets of chromosomes.

Emasculate: The removal of plant male sex organs or the inactivation of the organs with a chemical agent or a cytoplasmic or nuclear genetic factor conferring male sterility.

$F_1$ Hybrid: The first-generation progeny of the cross of two plants.

Genetic Complement: An aggregate of nucleotide sequences, the expression of which sequences defines the phenotype in corn plants, or components of plants including cells or tissue.

Genomic Estimated Breeding Value (GEBV): An estimation of genotyped populations using statistical model or models to predict the breeding values of a plant or plants.

Genomic Selection (GS) or Genome-wide selection (GWS): A use of genome-wide genotypic data to predict genomic estimated breeding values (GEBV) for selection purposes in breeding process.

Genotype: The genetic constitution of a cell or organism.

Haploid: A cell or organism having one set of the two sets of chromosomes in a diploid.

Isozymes: Detectable variants of an enzyme, the variants catalyzing the same reaction(s) but differing from each other, e.g., in primary structure and/or electrophoretic mobility. The differences between isozymes are under single gene, codominant control. Consequently, electrophoretic separation to produce band patterns can be equated to different alleles at the DNA level. Structural differences that do not alter charge cannot be detected by this method.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Marker assisted breeding or maker assisted selection (MAS): A process of selecting a desired trait or desired traits in a plant or plants by detecting one or more markers from the plant, where the marker is associated with the desired trait.

Phenotype: The detectable characteristics of a cell or organism in which the characteristics are the manifestation of gene expression.

Quantitative Trait Loci (QTL): Genetic loci that contribute, at least in part, certain numerically representable traits that are usually continuously distributed.

Regeneration: The development of a plant from tissue culture.

SSR profile: A profile of simple sequence repeats used as genetic markers and scored by gel electrophoresis following PCR amplification using flanking oligonucleotide primers.

Self-pollination: The transfer of pollen from the anther to the stigma of the same plant.

Single Locus Converted (Conversion) Plant: Plants that are developed by a plant breeding technique called back-crossing or by genome editing of a locus, wherein essentially all the morphological and physiological characteristics of an inbred are recovered in addition to the characteristics conferred by the single locus transferred into the inbred via the backcrossing or genome editing technique.

Three-way cross hybrid: A hybrid plant produced by crossing a first inbred plant with the $F_1$ hybrid progeny derived from crossing a second inbred plant with a third inbred plant.

Tissue Culture: A composition comprising isolated cells of the same or a different type or a collection of such cells organized into parts of a plant.

Transgene: A genetic sequence that has been introduced into the nuclear or chloroplast genome of a maize plant by a genetic transformation technique.

The following examples are included to demonstrate preferred embodiments. It should be appreciated by those of skill in the art that the techniques disclosed in the examples that follow represent techniques that function well in the practice of the present disclosure, and thus can be considered to constitute preferred modes for its practice. However, those of skill in the art should, considering the present disclosure, appreciate that many changes can be made in the specific embodiments that are disclosed and still obtain a like or similar result without departing from the spirit and scope of the appended claims.

Inbred Corn Plant CV962284

A. Origin and Breeding History

Inbred plant CV962284 was derived from a cross between the lines CV744222 and CV696879. The origin and breeding history of inbred plant CV962284 can be summarized as follows:

| Generation | Description |
| --- | --- |
| Cross | A crossed was made between two proprietary inbred lines. F1 seeds were bulked. |
| F1 | F1 plants were grown and self-pollinated. A F2 bulk selection was advanced. |
| F2 | F2 plants were grown and pollinated with a haploid inducer line in an induction nursery. A bulk of DH0 haploid kernels was formed. |
| DH0 | DH0 seeds were grown and self-pollinated. DH1 ear selections were saved from nursery row and bulked. |
| DH1 | DH1 seeds were grown and self-pollinated. DH2 ears were selected. The selection was coded as the designated inbred. |
| DH2 | DH2 ears were grown ear to row and self-pollinated. DH3 ear selections were saved. |
| DH3 | DH3 ears were grown ear to row and self-pollinated. DH4 ear selections were saved. |
| DH4 | DH4 ears were grown ear to row and self-pollinated. DH5 ear selections were saved. |
| DH5 | DH5 ears were grown ear to row and self-pollinated. DH6 ear selections were saved. |
| DH6 | DH6 ears were grown ear to row and self-pollinated. DH7 ear selections were saved. |
| DH7 | DH7 seeds was grown and self-pollinated. DH8 ear selections were saved and bulked. |

Corn variety CV962284 shows uniformity and stability within the limits of environmental influence for the traits described hereinafter in Table 1. CV962284 has been self-pollinated and ear-rowed enough generations with careful attention paid to uniformity of plant type to ensure homozygosity and phenotypic stability. No variant traits have been observed or are expected in CV962284.

Inbred corn plants can be reproduced by planting the seeds of the inbred corn plant CV962284, growing the resulting corn plants under self-pollinating or sib-pollinating conditions with adequate isolation using standard techniques well known to an artisan skilled in the agricultural arts. Seeds can be harvested from such a plant using standard, well known procedures.

B. Phenotypic Description

In accordance with another aspect of the present disclosure, there is provided a corn plant having the morphological characteristics of corn plant CV962284. A description of the morphological and physiological characteristics of corn plant CV962284 is presented in Table 1.

TABLE 1

| Morphological and Physiological Traits for Corn Variety CV962284 | | |
| --- | --- | --- |
| | CHARACTERISTIC | VALUE |
| 1 | STALK | |
| | Plant Height (cm) | 207.2 |
| | Ear Height (cm) | 66.9 |
| | Anthocyanin | BASAL WEAK |
| | Brace Root Color | MODERATE |
| | Internode Direction | STRAIGHT |
| | Internode Length (cm) | 18.3 |
| 2 | LEAF | |
| | Color | DARK GREEN |
| | Length (cm) | 73.1 |
| | Width (cm) | 8.5 |
| | Sheath Anthocyanin | BASAL WEAK |
| | Sheath Pubescence | LIGHT |
| | Marginal Waves | FEW |
| | Longitudinal Creases | FEW |
| 3 | TASSEL | |
| | Length (cm) | 42.3 |
| | Peduncle Length (cm) | 8.8 |
| | Branch Number | 8.3 |
| | Anther Color | YELLOW |

TABLE 1-continued

| Morphological and Physiological Traits for Corn Variety CV962284 | | |
| --- | --- | --- |
| | CHARACTERISTIC | VALUE |
| | Glume Color | GREEN |
| | Glume Band | ABSENT |
| 4 | EAR | |
| | Silk Color | YELLOW |
| | Number Per Stalk | 1 |
| | Position | UPRIGHT |
| | Length (cm) | 12.3 |
| | Shape | SEMI CONICAL |
| | Diameter (mm) | 44.3 |
| | Shank Length (cm) | 8.4 |
| | Husk Bract | SHORT |
| | Husk Cover (cm) | 5.8 |
| | Husk Opening | MODERATE |
| | Husk Color Fresh | GREEN |
| | Husk Color Dry | BUFF |
| | Cob Diameter (mm) | 28.2 |
| | Cob Color | RED |
| | Shelling Percent | 89.7 |
| 5 | KERNEL | |
| | Row Number | 15.3 |
| | Number Per Row | 26.1 |
| | Row Direction | SLIGHTLY CURVED |
| | Type | DENT |
| | Cap Color | DEEP YELLOW |
| | Side Color | DEEP YELLOW |
| | Length (depth) (mm) | 10.2 |
| | Width (mm) | 7.6 |
| | Thickness (mm) | 5.5 |
| | Endosperm Type | NORMAL |
| | Endosperm Color | YELLOW |

*These are typical values. Values may vary due to environment. Other values that are substantially equivalent are within the scope of the disclosure. Substantially equivalent refers to quantitative traits that when compared do not show statistical differences of their means.

C. Deposit Information

A deposit was made of at least 625 seeds of corn variety CV962284 with the Provasoli-Guillard National Center for Marine Algae and Microbiota (NCMA) at Bigelow Laboratory for Ocean Sciences, 60 Bigelow Drive, East Boothbay, ME 04544 USA. The deposit was assigned NCMA Accession No. 202306062. The date of deposit of the seeds with the NCMA was Jun. 15, 2023. All restrictions upon availability of the deposit to the public will be irrevocably removed upon granting of the patent, and the deposit is intended to meet all the requirements of the Budapest Treaty and 37 C.F.R. § 1.801-1.809. Access to this deposit will be available during the pendency of the application to the Commissioner of Patents and Trademarks and persons determined by the Commissioner to be entitled thereto upon request. The deposit has been accepted under the Budapest Treaty and will be maintained in the NCMA Depositary, which is a public depositary, for a period of 30 years, or 5 years after the most recent request, or for the enforceable life of the patent, whichever is longer, and will be replaced if it becomes nonviable during that period. Applicant does not waive any infringement of their rights granted under this patent or under the Plant Variety Protection Act (7 U.S.C. 2321 et seq.).

Further Embodiments

In one embodiment, compositions are provided comprising a seed of corn variety CV962284 comprised in plant seed growth media. Plant seed growth media are well known to those of skill in the art and include, but are in no way limited to, soil or synthetic cultivation medium. Plant seed growth media can provide adequate physical support for seeds and can retain moisture and/or nutritional components.

In certain further aspects, the disclosure provides plants modified to include at least a first desired heritable trait. Such plants may, in one embodiment, be developed by a plant breeding technique called backcrossing, wherein essentially all the morphological and physiological characteristics of a variety are recovered in addition to a genetic locus transferred into the plant via the backcrossing technique. By essentially all the morphological and physiological characteristics, it is meant that the characteristics of a plant are recovered that are otherwise present when compared in the same environment, other than an occasional variant trait that might arise during backcrossing or direct introduction of a transgene. It is understood that a locus introduced by backcrossing may or may not be transgenic in origin, and thus the term backcrossing specifically includes backcrossing to introduce loci that were created by genetic transformation.

Backcrossing methods can be used with the present disclosure to improve or introduce a trait into a variety. The term backcrossing as used herein refers to the repeated crossing of a hybrid progeny back to one of the parental corn plants. The parental corn plant that contributes the locus or loci for the desired trait is termed the nonrecurrent or donor parent. This terminology refers to the fact that the nonrecurrent parent is used one time in the backcross protocol and therefore does not recur.

The parental corn plant to which the locus or loci from the nonrecurrent parent are transferred is known as the recurrent parent as it is used for several rounds in the backcrossing protocol. In a typical backcross protocol, the original parent of interest (recurrent parent) is crossed to a second variety (nonrecurrent parent) that carries the genetic locus of interest to be transferred. The resulting progeny from this cross are then crossed again to the recurrent parent and the process is repeated until a corn plant is obtained wherein essentially all the morphological and physiological characteristics of the recurrent parent are recovered in the converted plant, in addition to the transferred locus from the nonrecurrent parent. The backcross process may be accelerated using genetic markers, such as SSR, RFLP, SNP or AFLP markers to identify plants with the greatest genetic complement from the recurrent parent.

The selection of a suitable recurrent parent is a key step for a successful backcrossing procedure. The goal of a backcross protocol is to add or substitute one or more new traits in the original variety and progeny therefrom. To accomplish this, a genetic locus of the recurrent parent is modified or substituted with the desired locus from the nonrecurrent parent, while retaining essentially all the rest of the genetic, and therefore the morphological and physiological constitution of the original plant. The choice of the nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many traits have been identified that are not regularly selected for in the development of a new variety but that can be improved by backcrossing techniques. A genetic locus conferring the traits may or may not be transgenic. Examples of such traits known to those of skill in the art include, but are not limited to, male sterility, waxy starch, herbicide resistance, resistance for bacterial, fungal, or viral disease, insect resistance, male fertility and enhanced nutritional quality. These genes are inherited through the nucleus but may be inherited through the cytoplasm. Some known exceptions to this are genes for male sterility, which can be inherited cytoplasmically but act as a single locus trait.

Direct selection may be applied when a genetic locus acts as a dominant trait. An example of a dominant trait is the herbicide resistance trait. For this selection process, the progeny of the initial cross are sprayed with the herbicide prior to the backcrossing. The spraying eliminates any plants that do not have the desired herbicide resistance character-istic, and only those plants that have the herbicide resistance gene are used in the subsequent backcross. This process is then repeated for all additional backcross generations.

Many useful traits are introduced by genetic transforma-tion techniques. Methods for the genetic transformation of corn are known to those of skill in the art.

Included among various plant transformation techniques are methods that permit the site-specific modification of a plant genome. These modifications can include, but are not limited to, site-specific mutations, deletions, insertions, and replacements of nucleotides. These modifications can be made anywhere within the genome of a plant, for example, in genomic elements, including, among others, coding sequences, regulatory elements, and non-coding DNA sequences. Such methods may be used to modify a particular trait conferred by a locus. The techniques for making such modifications by genome editing are well known in the art and include, for example, use of CRISPR-Cas systems, zinc-finger nucleases (ZFNs), and transcription activator-like effector nucleases (TALENs), among others. A site-specific nuclease provided herein may be selected from the group consisting of a zinc-finger nuclease (ZFN), a mega-nuclease, an RNA-guided endonuclease, a TALE-endonu-clease (TALEN), a recombinase, a transposase, or any combination thereof. A recombinase may be a serine recom-binase attached to a DNA recognition motif, a tyrosine recombinase attached to a DNA recognition motif or other recombinase enzyme known in the art. A recombinase or transposase may be a DNA transposase or recombinase attached to a DNA binding domain. A tyrosine recombinase attached to a DNA recognition motif may be selected from the group consisting of a Cre recombinase, a Flp recombi-nase, and a Tnp1 recombinase. According to some embodi-ments, a Cre recombinase or a Gin recombinase provided herein is tethered to a zinc-finger DNA binding domain. In another embodiment, a serine recombinase attached to a DNA recognition motif provided herein is selected from the group consisting of a PhiC31 integrase, an R4 integrase, and a TP-901 integrase. In another embodiment, a DNA trans-posase attached to a DNA binding domain provided herein is selected from the group consisting of a TALE-piggyBac and TALE-Mutator. An RNA-guided endonuclease may be selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, and homologs or modified versions thereof, Argonaute (non-limiting examples of Argonaute proteins include Thermus thermo-philus Argonaute (TtAgo), Pyrococcus furiosus Argonaute (PfAgo), Natronobacterium gregoryi Argonaute (NgAgo) and homologs or modified versions thereof. According to some embodiments, an RNA-guided endonuclease may be a Cas9 or Cpf1 enzyme.

It is understood to those of skill in the art that a transgene need not be directly transformed into a plant, as techniques to produce stably transformed corn plants that pass single loci to progeny by Mendelian inheritance are well known in the art. Such loci may therefore be passed from parent plant to progeny plants by standard plant breeding techniques that are well known in the art. Non-limiting examples of traits that may be introduced into a corn plant according to specific embodiments are provided below.

A. Male Sterility

Male sterility genes can increase the efficiency with which hybrids are made, in that they eliminate the need to physi-cally emasculate the corn plant used as a female in each cross. Examples of genes conferring male sterility and herbicide-inducible male sterility genes are well known in the art.

Where one desires to employ male-sterility systems with a corn plant in accordance with the disclosure, it may be beneficial to also utilize one or more male-fertility restorer genes. For example, when cytoplasmic male sterility (CMS) is used, hybrid seed production requires three inbred lines: (1) a cytoplasmically male-sterile line having a CMS cyto-plasm; (2) a fertile inbred with normal cytoplasm, which is isogenic with the CMS line for nuclear genes ("maintainer line"); and (3) a distinct, fertile inbred with normal cyto-plasm, carrying a fertility restoring gene ("restorer" line). The CMS line is propagated by pollination with the main-tainer line, with all the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful when the vegetative tissue of the corn plant is utilized, e.g., for silage, but in most cases, the seeds will be deemed the most valuable portion of the crop, so fertility of the hybrids in these crops must be restored. Therefore, one aspect of the current disclosure concerns plants of the corn variety CV962284 comprising a genetic locus capable of restoring male fertility in an oth-erwise male-sterile plant. Examples of male-sterility genes and corresponding restorers that could be employed with the plants of the disclosure are well known to those of skill in the art of plant breeding.

B. Herbicide Resistance

Numerous herbicide resistance genes are known and may be employed with the disclosure. A non-limiting example is a gene conferring resistance to an herbicide that inhibits the growing point or meristem such as imidazolinone or sulfo-nylurea herbicides. As imidazolinone and sulfonylurea her-bicides are acetolactate synthase (ALS)-inhibiting herbi-cides that prevent the formation of branched chain amino acids are well known to those of skill in the art. As a non-limiting example, a gene may be employed to confer resistance to the exemplary sulfonylurea herbicide nicosul-furon.

Resistance genes for glyphosate (resistance conferred by mutant 5-enolpyruvylshikimate-3-phosphate synthase (EPSPS) and aroA genes, respectively) and other phosphono compounds such as glufosinate (phosphinothricin acetyltransferase (PAT) and *Streptomyces hygroscopicus* phosphinothricin acetyltransferase (bar) genes) may also be used. As a non-limiting example, a gene may confer resistance to other exemplary phenoxy class herbicides that include, but are not limited to, quizalofop-p-ethyl and 2,4-dichlorophenoxyacetic acid (2,4-D).

Genes are also known that confer resistance to herbicides that inhibit photosynthesis such as, for example, triazine herbicides (psbA and gs+ genes) and benzonitrile herbicides (nitrilase gene). As a non-limiting example, a gene may confer resistance to the exemplary benzonitrile herbicide bromoxynil.

C. Waxy Starch

The waxy characteristic is an example of a recessive trait. In this example, the progeny resulting from the first backcross generation ($BC_1$) must be grown and selfed. A test is then run on the selfed seed from the $BC_1$ plant to determine which $BC_1$ plants carried the recessive gene for the waxy trait. In other recessive traits additional progeny testing, for example growing additional generations such as the $BC_1F_1$, may be required to determine which plants carry the recessive gene.

D. Disease and Pest Resistance

Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains.

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus.

E. Insect Resistance

One example of an insect resistance gene includes a *Bacillus thuringiensis* (Bt) protein, a derivative thereof or a synthetic polypeptide modeled thereon. Yet another insect resistance gene is an enzyme inhibitor, for example, a protease or proteinase inhibitor or an amylase inhibitor. An insect-specific hormone or pheromone may also be used. Still other examples include an insect-specific antibody, or an immunotoxin derived therefrom and a developmental-arrestive protein.

F. Modified Fatty Acid, Phytate, and Carbohydrate Metabolism

Genes may be used conferring modified fatty acid metabolism, in terms of content and quality. Oil and fatty acid composition content and production may be modified.

Phytate metabolism may also be modified by introduction of a phytase-encoding gene to enhance breakdown of phytate, adding more free phosphate to the transformed plant. In corn, this, for example, could be accomplished by cloning and then reintroducing DNA associated with the single allele that is responsible for corn mutants characterized by low levels of phytic acid.

A number of genes are known that may be used to alter carbohydrate metabolism. For example, plants may be transformed with a gene coding for an enzyme that alters the branching pattern of starch.

Abiotic stress includes dehydration or other osmotic stress, salinity, high or low light intensity, high or low temperatures, submergence, exposure to heavy metals, and oxidative stress. Delta-pyrroline-5-carboxylate synthetase (P5CS) from mothbean has been used to provide protection against general osmotic stress. Mannitol-1-phosphate dehydrogenase (mt1D) from *E. coli* has been used to provide protection against drought and salinity. Choline oxidase (codA from *Arthrobactor globiformis*) can protect against cold and salt. *E. coli* choline dehydrogenase (betA) provides protection against salt. Additional protection from cold can be provided by omega-3-fatty acid desaturase (fad7) from *Arabidopsis thaliana*.

G. Additional Traits

Additional traits can be introduced into the corn variety of the present disclosure. A non-limiting example of such a trait is a coding sequence that decreases RNA and/or protein levels. The decreased RNA and/or protein levels may be achieved through RNAi methods.

Another trait that may find use with the corn variety is a sequence that allows for site-specific recombination. The recombinase genes can be encoded at any location within the genome of the corn plant and are active in the hemizygous state.

It may also be desirable to make corn plants more tolerant to or more easily transformed with *Agrobacterium tumefaciens*. Expression of p53 and iap, two baculovirus cell-death suppressor genes, inhibited tissue necrosis and DNA cleavage. Additional targets can include plant-encoded proteins that interact with the *Agrobacterium* Vir genes; enzymes involved in plant cell wall formation; and histones, histone acetyltransferases and histone deacetylases.

In addition to the modification of oil, fatty acid or phytate content described above, it may additionally be beneficial to modify the amounts or levels of other compounds. For example, the amount or composition of antioxidants can be altered.

Additionally, seed amino acid content may be manipulated and is well known in the art.

It may be beneficial to modify the corn plant height. Short stature corn has stronger stalks due to the reduced height, which are less likely to break or fall over in high winds. Shorter plants also make the corn fields more accessible to standard ground equipment longer into the growing season, creating the opportunity for more timely, precise applications of crop protection products and other inputs. Short stature corn may be produced via techniques including but not limited to conventional breeding, biotechnology, and gene editing techniques. Corn plants comprising non-natural brachytic mutations results in plants with reduced height. Additionally, short stature corn may be produced by altering the plant's gibberellin metabolism via suppression, mutagenesis and/or editing of specific gibberellin oxidase genes. Techniques for manipulating corn height are well known in the art.

H. Origin and Breeding History of an Exemplary Introduced Trait

85DGD1 MLms is a conversion of 85DGD1 to cytoplasmic male sterility. 85DGD1 MLms was derived using backcross methods. 85DGD1 (a proprietary inbred of Monsanto Company) was used as the recurrent parent and MLms, a germplasm source carrying ML cytoplasmic sterility, was used as the nonrecurrent parent. The breeding history of the converted inbred 85DGD1 MLms can be summarized as follows:

| Hawaii Nurseries Planting Date Apr. 2, 1992 | Made up S-O: Female row 585 male row 500 |
|---|---|
| Hawaii Nurseries Planting Date Jul. 15, 1992 | S-O was grown, and plants were backcrossed times 85DGD1 (rows 444 ' 443) |
| Hawaii Nurseries Planting Date Nov. 18, 1992 | Bulked seed of the BC$_1$ was grown and backcrossed times 85DGD1 (rows V3-27 ' V3-26) |
| Hawaii Nurseries Planting Date Apr. 2, 1993 | Bulked seed of the BC$_2$ was grown and backcrossed times 85DGD1 (rows 37 ' 36) |
| Hawaii Nurseries Planting Date Jul. 14, 1993 | Bulked seed of the BC$_3$ was grown and backcrossed times 85DGD1 (rows 99 ' 98) |
| Hawaii Nurseries Planting Date Oct. 28, 1993 | Bulked seed of BC$_4$ was grown and backcrossed times 85DGD1 (rows KS-63 ' KS-62) |
| Summer 1994 | A single ear of the BC$_5$ was grown and backcrossed times 85DGD1 (MC94-822 ' MC94-822-7) |
| Winter 1994 | Bulked seed of the BC$_6$ was grown and backcrossed times 85DGD1 (3Q-1 ' 3Q-2) |
| Summer 1995 | Seed of the BC$_7$ was bulked and named 85DGD1 MLms. |

I. Illustrative Procedures for Introduction of a Desired Trait

As described above, techniques to produce corn plants with added traits are well known in the art A non-limiting example of such a procedure one of skill in the art would use for preparation of a corn plant of CV962284 comprising an added trait is as follows:

(a) crossing corn plant CV962284 to a second (nonrecurrent) corn plant comprising a locus to be converted in corn plant CV962284;

(b) selecting at least a first progeny plant resulting from the crossing and comprising the locus;

(c) crossing the selected progeny to corn plant CV962284; and (d) repeating steps (b) and (c) until a plant of variety CV962284 is obtained comprising the locus.

Following these steps, essentially any locus may be introduced into corn variety CV962284. For example, molecular techniques allow introduction of any given locus, without the need for phenotypic screening of progeny during the backcrossing steps.

PCR and Southern hybridization are two examples of molecular techniques that may be used for confirmation of the presence of a given locus and thus conversion of that locus. The techniques are carried out as follows: Approximately one gram of leaf tissue is lyophilized overnight in 15 ml polypropylene tubes. Freeze-dried tissue is ground to a powder in the tube using a glass rod. Powdered tissue is mixed thoroughly with 3 ml extraction buffer (7.0 M urea, 0.35 M NaCl, 0.05 M Tris-HCl pH 8.0, 0.01 M EDTA, 1% sarcosine). Tissue/buffer homogenate is extracted with 3 ml phenol/chloroform. The aqueous phase is separated by centrifugation and precipitated twice using 1/10 volume of 4.4 M ammonium acetate, pH 5.2, and an equal volume of isopropanol. The precipitate is washed with 75% ethanol and resuspended in 100-500 µl TE (0.01 M Tris-HC1, 0.001 M EDTA, pH 8.0). The DNA may then be screened as desired for presence of the locus.

For PCR, 200-1000 ng genomic DNA from the progeny plant being screened is added to a reaction mix containing 10 mM Tris-HCl, pH 8.3, 1.5 mM MgCl$_2$, 50 mM KCl, 0.1 mg/ml gelatin, 200 µM each dATP, dCTP, dGTP, dTTP, 20% glycerol, 2.5 units Taq DNA polymerase and 0.5 µM each of forward and reverse DNA primers that span a segment of the locus being converted. The reaction is run in a thermal cycling machine 3 minutes at 94 C, 39 repeats of the cycle 1 minute at 94 C, 1 minute at 50 C, 30 seconds at 72° C., followed by 5 minutes at 72° C. Twenty µl of each reaction mix is run on a 3.5% NuSieve gel in TBE buffer (90 mM Tris-borate, 2 mM EDTA) at 50 V for two to four hours. The amplified fragment is detected using an agarose gel. Detection of an amplified fragment corresponding to the segment of the locus spanned by the primers indicates the presence of the locus.

For Southern analysis, plant DNA is restricted, separated in an agarose gel, and transferred to a Nylon filter in 10× SCP (20 SCP: 2 M NaCl, 0.6 M disodium phosphate, 0.02 M disodium EDTA) according to standard methods. Locus DNA or RNA sequences are labeled, for example, radioactively with $^{32}$P by random priming. Filters are prehybridized in 6× SCP, 10% dextran sulfate, 2% sarcosine, and 500 µg/ml denatured salmon sperm DNA. The labeled probe is denatured, hybridized to the filter, and washed in 2× SCP, 1% SDS at 65° C. for 30 minutes and visualized by autoradiography using Kodak XAR5 film. Presence of the locus is indicated by detection of restriction fragments of the appropriate size.

Tissue Cultures and in Vitro Regeneration of Corn Plants

A further aspect relates to tissue cultures of the corn plant designated CV962284. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, pollen, flowers, kernels, ears, cobs, leaves, husks, stalks, roots, root tips, anthers, silk, and the like. In a preferred embodiment, the tissue culture comprises embryos, protoplasts, meristematic cells, pollen, leaves, or anthers derived from immature tissues of these plant parts. Means for preparing and maintaining plant tissue cultures are well known in the art. By way of example, a tissue culture comprising organs such as tassels or anthers has been used to produce regenerated plants.

One type of tissue culture is tassel/anther culture. Tassels contain anthers that in turn enclose microspores. Microspores develop into pollen. For anther/microspore culture, if tassels are the plant composition, they are preferably selected at a stage when the microspores are uninucleate, that is, include only one, rather than 2 or 3 nuclei. Methods to determine the correct stage are well known to those skilled in the art and include mitramycin fluorescent staining trypan blue (preferred) and acetocarmine squashing. The mid-uninucleate microspore stage has been found to be the developmental stage most responsive to the subsequent methods disclosed to produce plants.

Although microspore-containing plant organs such as tassels can be pretreated at any cold temperature below about 25° C., a range of 4 to 25° C. is preferred, and a range of 8 to 14° C. is particularly preferred. Although other temperatures yield embryoids and regenerated plants, cold temperatures produce optimum response rates compared to pretreatment at temperatures outside the preferred range. Response rate is measured as either the number of embryoids or the number of regenerated plants per number of microspores initiated in culture. Exemplary methods of microspore culture are well known in the art.

Although not required, when tassels are employed as the plant organ, it is preferred to sterilize their surface. Following surface sterilization of the tassels, for example, with a solution of calcium hypochloride, the anthers are removed from about 70 to 150 spikelets (small portions of the tassels) and placed in a preculture or pretreatment medium. Larger or smaller amounts can be used depending on the number of anthers.

When one elects to employ tassels directly, tassels are preferably pretreated at a cold temperature for a predefined time, preferably at 10° C. for about 4 days. After pretreatment of a whole tassel at a cold temperature, dissected anthers are further pretreated in an environment that diverts microspores from their developmental pathway. The function of the preculture medium is to switch the developmental program from one of pollen development to that of embryoid/callus development. An embodiment of such an environment in the form of a preculture medium includes a sugar alcohol, for example mannitol or sorbitol, inositol, or the like. An exemplary synergistic combination is the use of mannitol at a temperature of about 10° C. for a period ranging from about 10 to 14 days. In a preferred embodiment, 3 ml of 0.3 M mannitol combined with 50 mg/l of ascorbic acid, silver nitrate, and colchicine is used for incubation of anthers at 10° C. for between 10 and 14 days. Another embodiment is to substitute sorbitol for mannitol. The colchicine produces chromosome doubling at this early stage. The chromosome doubling agent is preferably only present at the preculture stage.

It is believed that the mannitol or other similar carbon structure or environmental stress induces starvation and functions to force microspores to focus their energies on entering developmental stages. The cells are unable to use, for example, mannitol as a carbon source at this stage. It is believed that these treatments confuse the cells causing them to develop as embryoids and plants from microspores. Dramatic increases in development from these haploid cells, as high as 25 embryoids in $10^4$ microspores, have resulted from using these methods.

To isolate microspores, an isolation media is preferred. An isolation media is used to separate microspores from the anther walls while maintaining their viability and embryogenic potential. An illustrative embodiment of an isolation media includes a 6% sucrose or maltose solution combined with an antioxidant such as 50 mg/l of ascorbic acid, 0.1 mg/l biotin, and 400 mg/l of proline, combined with 10 mg/l of nicotinic acid and 0.5 mg/l AgNO$_3$. In another embodiment, the biotin and proline are omitted.

An isolation media preferably has a higher antioxidant level when it is used to isolate microspores from a donor plant, a plant from which a plant composition containing a microspore is obtained, that is field grown in contrast to greenhouse grown. A preferred level of ascorbic acid in an isolation medium is from about 50 mg/l to about 125 mg/l and, more preferably, from about 50 mg/l to about 100 mg/l.

One can find particular benefit in employing a support for the microspores during culturing and subculturing. Any support that maintains the cells near the surface can be used. An illustrative embodiment of a solid support is a TRANSWELL® culture dish. Another embodiment of a solid support for development of the microspores is a bilayer plate wherein liquid media is on top of a solid base. Other embodiments include a mesh or a millipore filter. Preferably, a solid support is a nylon mesh in the shape of a raft. A raft is defined as an approximately circular support material that is capable of floating slightly above the bottom of a tissue culture vessel, for example, a petri dish, of about a 60- or 100-mm size, although any other laboratory tissue culture vessel will suffice. In an illustrative embodiment, a raft is about 55 mm in diameter.

Culturing isolated microspores on a solid support, for example, on a 10 mm pore nylon raft floating on 2.2 ml of medium in a 60 mm petri dish, prevents microspores from sinking into the liquid medium and thus avoiding low oxygen tension. These types of cell supports enable the serial transfer of the nylon raft with its associated microspore/embryoids to full strength medium containing activated charcoal and solidified with, for example, GELRITE™ (solidifying agent).

The liquid medium passes through the mesh while the microspores are retained and supported at the medium-air interface. The surface tension of the liquid medium in the petri dish causes the raft to float. The liquid can pass through the mesh; consequently, the microspores stay on top. The mesh remains on top of the total volume of liquid medium.

The culture vessels can be further defined as either (1) a bilayer 60 mm petri plate wherein the bottom 2 ml of medium are solidified with 0.7% agarose overlaid with 1 mm of liquid containing the microspores; (2) a nylon mesh raft wherein a wafer of nylon is floated on 1.2 ml of medium and 1 ml of isolated microspores is pipetted on top; or (3) TRANSWELL® plates wherein isolated microspores are pipetted onto membrane inserts that support the microspores at the surface of 2 ml of medium.

Examples of processes of tissue culturing and regeneration of corn are well known in the art.

Processes of Crossing Corn Plants and the Corn Plants Produced by Such Crosses The present disclosure provides processes of preparing novel corn plants and corn plants produced by such processes. In accordance with such a process, a first parent corn plant may be crossed with a second parent corn plant wherein at least one of the first and second corn plants is the inbred corn plant CV962284. One application of the process is in the production of F$_1$ hybrid plants. Another important aspect of this process is that it can be used for the development of novel inbred lines. For example, the inbred corn plant CV962284 could be crossed to any second plant, and the resulting hybrid progeny each selfed for about 5 to 7 or more generations, thereby providing a large number of distinct, pure-breeding inbred lines. These inbred lines could then be crossed with other inbred or non-inbred lines and the resulting hybrid progeny analyzed for beneficial characteristics. In this way, novel inbred lines conferring desirable characteristics could be identified.

Corn plants (*Zea mays* L.) can be crossed by either natural or mechanical techniques. Natural pollination occurs in corn when wind blows pollen from the tassels to the silks that protrude from the tops of the recipient ears. Mechanical pollination can be affected either by controlling the types of pollen that can blow onto the silks or by pollinating by hand. In one embodiment, crossing comprises the steps of:

(a) planting in pollinating proximity seeds of a first and a second parent corn plant, and preferably, seeds of a first inbred corn plant and a second, distinct inbred corn plant;

(b) cultivating or growing the seeds of the first and second parent corn plants into plants that bear flowers;

(c) emasculating flowers of either the first or second parent corn plant, i.e., treating the flowers to prevent pollen production, or alternatively, using as the female parent a male sterile plant, thereby providing an emasculated parent corn plant;

(d) allowing natural cross-pollination to occur between the first and second parent corn plants;

(e) harvesting seeds produced on the emasculated parent corn plant; and, when desired, (f) growing the harvested seed into a corn plant, preferably, a hybrid corn plant.

Parental plants are typically planted in pollinating proximity to each other by planting the parental plants in alternating rows, in blocks or in any other convenient planting pattern. Where the parental plants differ in timing of sexual maturity, it may be desired to plant the slower maturing plant first, thereby ensuring the availability of pollen from the male parent during the time at which silks on the female parent are receptive to pollen. Plants of both parental parents are cultivated and allowed to grow until the time of flowering. Advantageously, during this growth stage, plants are in general treated with fertilizer and/or other agricultural chemicals as considered appropriate by the grower.

At the time of flowering, if plant CV962284 is employed as the male parent, the tassels of the other parental plant are removed from all plants employed as the female parental plant to avoid self-pollination. The detasseling can be achieved manually but also can be done by machine, if desired. Alternatively, when the female parent corn plant comprises a cytoplasmic or nuclear gene conferring male sterility, detasseling may not be required. Additionally, a chemical gametocide may be used to sterilize the male flowers of the female plant. In this case, the parent plants used as the male may either not be treated with the chemical agent or may comprise a genetic factor that causes resistance to the emasculating effects of the chemical agent. Gametocides affect processes or cells involved in the development, maturation, or release of pollen. Plants treated with such gametocides are rendered male sterile, but typically remain female fertile. The use of chemical gametocides are well known in the art. Furthermore, the use of glyphosate herbicide to produce male sterile corn plants are well known in the art.

Following emasculation, the plants are then typically allowed to continue to grow, and natural cross-pollination occurs because of the action of wind, which is normal in the pollination of grasses, including corn. As a result of the emasculation of the female parent plant, all the pollen from the male parent plant is available for pollination because tassels, and thereby pollen bearing flowering parts, have been previously removed from all plants of the inbred plant being used as the female in the hybridization. Of course, during this hybridization procedure, the parental varieties are grown such that they are isolated from other corn fields to minimize or prevent any accidental contamination of pollen from foreign sources. These isolation techniques are well within the skill of those skilled in this art.

Both parental inbred plants of corn may be allowed to continue to grow until maturity or the male rows may be destroyed after flowering is complete. Only the ears from the female inbred parental plants are harvested to obtain seeds of a novel $F_1$ hybrid. The novel $F_1$ hybrid seed produced can then be planted in a subsequent growing season in commercial fields or, alternatively, advanced in breeding protocols for purposes of developing novel inbred lines.

Alternatively, in another embodiment, both first and second parent corn plants can be from variety CV962284. Thus, any corn plant produced using corn plant CV962284 forms a part of the disclosure. As used herein, crossing can mean selfing, backcrossing, crossing to another or the same inbred, crossing to populations, and the like. All corn plants produced using the inbred corn plant CV962284 as a parent are, therefore, within the scope of this disclosure.

J. $F_1$ Hybrid Corn Plant and Seed Production

One beneficial use of the instant corn variety is in the production of hybrid seed. Any time the inbred corn plant CV962284 is crossed with another, different, corn inbred, a first generation ($F_1$) corn hybrid plant is produced. As such, an $F_1$ hybrid corn plant can be produced by crossing CV962284 with any second inbred maize plant. Essentially any other corn plant can be used to produce a hybrid corn plant having corn plant CV962284 as one parent. All that is required is that the second plant be fertile, which corn plants naturally are, and that the plant is not corn variety CV962284.

The goal of the process of producing an $F_1$ hybrid is to manipulate the genetic complement of corn to generate new combinations of genes that interact to yield new or improved traits (phenotypic characteristics). A process of producing an $F_1$ hybrid typically begins with the production of one or more inbred plants. Those plants are produced by repeated crossing of ancestrally related corn plants to try to combine certain genes within the inbred plants.

Corn has a diploid phase, which means two conditions of a gene (two alleles) occupy each locus (position on a chromosome). If the alleles are the same at a locus, there is said to be homozygosity. If they are different, there is said to be heterozygosity. In a completely inbred plant, all loci are homozygous. Because many loci when homozygous are deleterious to the plant, leading to reduced vigor, less kernels, weak and/or poor growth, production of inbred plants is an unpredictable and arduous process. Under some conditions, heterozygous advantage at some loci effectively bars perpetuation of homozygosity.

A single cross hybrid corn variety is the cross of two inbred plants, each of which has a genotype that complements the genotype of the other. Typically, $F_1$ hybrids are more vigorous than their inbred parents. This hybrid vigor, or heterosis, is manifested in many polygenic traits, including markedly improved yields, better stalks, better roots, better uniformity and better insect and disease resistance. In the development of hybrids only the $F_1$ hybrid plants are typically sought. An $F_1$ single cross hybrid is produced when two inbred plants are crossed. A double cross hybrid is produced from four inbred plants crossed in pairs (A×B and C×D) and then the two $F_1$ hybrids are crossed again (A×B)× (C×D). A three-way cross hybrid is produced from three distinct inbred plants. First, two of those three inbred plants are crossed to generate $F_1$ hybrid progeny. That $F_1$ hybrid progeny is then crossed with the third inbred plant to yield the triple cross hybrid progeny.

Thousands of corn varieties are known to those of skill in the art, any one of which could be crossed with corn plant CV962284 to produce a hybrid plant.

An example of an $F_1$ hybrid that has been produced with CV962284 as a parent is the hybrid CH010459. Hybrid CH010459 was produced by crossing inbred corn plant CV962284 with the inbred corn plant designated CV874402 (U.S. patent application Ser. No. 17/987,025, the disclosure of which is specifically incorporated herein by reference in its entirety).

When the inbred corn plant CV962284 is crossed with another inbred plant to yield a hybrid, it can serve as either the maternal or paternal plant. For many crosses, the outcome is the same regardless of the assigned sex of the parental plants. Depending on the seed production characteristics relative to a second parent in a hybrid cross, it may be desired to use one of the parental plants as the male or female parent. Some plants produce tighter ear husks leading to more loss, for example due to rot. There can be delays in silk formation, which deleteriously affects the timing of the reproductive cycle for a pair of parental plants. Seed coat characteristics can be preferable in one plant. Pollen can be shed better by one plant. Therefore, a decision to use one parent plant as a male or female may be made based on any such characteristics as is well known to those of skill in the art.

K. Development of Corn Varieties

The development of new varieties using one or more starting varieties is well known in the art. In accordance with the disclosure, novel varieties may be created by crossing corn variety CV962284 followed by multiple generations of breeding according to such well known methods. New varieties may be created by crossing corn variety CV962284 with any second plant. In selecting such a second plant to cross for the purpose of developing novel inbred lines, it may be desired to choose those plants that either themselves exhibit one or more selected desirable characteristics or exhibit the desired characteristic(s) when in hybrid combination. Examples of potentially desired characteristics include greater yield, better stalks, better roots, resistance to insecticides, herbicides, pests, and disease, tolerance to heat and drought, reduced time to crop maturity, better agronomic quality, higher nutritional value, and uniformity in germination times, stand establishment, growth rate, maturity, and fruit size.

Once initial crosses have been made with corn variety CV962284, inbreeding takes place to produce new inbred varieties. Inbreeding requires manipulation by human breeders. Even in the extremely unlikely event inbreeding rather than crossbreeding occurred in natural corn, achievement of complete inbreeding cannot be expected in nature due to well-known deleterious effects of homozygosity and the considerable number of generations the plant would have to breed in isolation. The reason for the breeder to create inbred plants is to have a known reservoir of genes whose gametic transmission is predictable.

The pedigree breeding method involves crossing two genotypes. Each genotype can have one or more desirable characteristics lacking in the other; or each genotype can complement the other. If the two original parental genotypes do not provide all the desired characteristics, other genotypes can be included in the breeding population. Superior plants that are the products of these crosses are selfed and selected in successive generations. Each succeeding generation becomes more homogeneous because of self-pollination and selection. Typically, this method of breeding involves five or more generations of selfing and selection: $F_1 \rightarrow F_2$; $F_2 \rightarrow F_3$; $F_3 \rightarrow F_4$; $F_4 \rightarrow F_5$, etc. After at least five generations, the inbred plant is considered genetically pure.

Marker assisted selection (MAS) can be used to reduce the number of breeding cycles and improve selection accuracy. Genome-wide selection (GWS)/genomic selection (GS) can also be used as an alternative to, or in combination to, marker assisted selection and phenotype selection. GS utilizes quantitative models over a large number of markers distributed across the genome to predict the genomic estimated breeding values (GEBVs) of individual plants that has been genotyped but not phenotyped. GS can improve complex traits or combination of multiple traits without the need to identify markers associated with the traits. GS can replace phenotyping in a few selection cycles, thus reducing the cost and the time required for variety development.

Uniform lines of new varieties may also be developed by way of double haploids. This technique allows the creation of true breeding lines without the need for multiple generations of selfing and selection. In this manner true breeding lines can be produced in as little as one generation. Haploid induction systems have been developed for various plants to produce haploid tissues, plants, and seeds. The haploid induction system can produce haploid plants from any genotype by crossing with an inducer line. Inducer lines and methods for obtaining haploid plants are known in the art.

Haploid embryos may be produced, for example, from microspores, pollen, anther cultures, or ovary cultures. The haploid embryos may then be doubled autonomously, or by chemical treatments (e.g., colchicine treatment). Alternatively, haploid embryos may be grown into haploid plants and treated to induce chromosome doubling. In either case, fertile homozygous plants are obtained. In accordance with the disclosure, any of such techniques may be used in connection with a plant and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred but are like the superior parent for most or all other loci. The last backcross generation would be selfed to give pure breeding progeny for the trait being transferred.

The development of a hybrid corn variety involves three steps: (1) the selection of plants from various germplasm pools; (2) the selfing of the selected plants for several generations to produce a series of inbred plants, which each breed true and are highly uniform; and (3) crossing the selected inbred plants with unrelated inbred plants to produce the hybrid progeny ($F_1$). During the inbreeding process in corn, the vigor of the plants decreases. Vigor is restored when two unrelated inbred plants are crossed to produce the hybrid progeny ($F_1$). An important consequence of the homozygosity and homogeneity of the inbred plants is that the hybrid between any two inbreds is always the same. Once the inbreds that give a superior hybrid have been identified, hybrid seed can be reproduced indefinitely if the homogeneity of the inbred parents is maintained. Conversely, much of the hybrid vigor exhibited by $F_1$ hybrids is lost in the next generation ($F_2$). Consequently, seed from hybrid varieties is not used for planting stock. It is not beneficial for farmers to save seed of $F_1$ hybrids. Rather, farmers purchase $F_1$ hybrid seed for planting every year.

The development of inbred plants requires at least about 5 to 7 generations of selfing. Inbred plants are then cross bred to develop improved $F_1$ hybrids. Hybrids are then screened and evaluated in small scale field trials. Typically, about 10 to 15 phenotypic traits, selected for their potential commercial value, are measured. A selection index of the most commercially important traits is used to help evaluate hybrids. FACT, an acronym for Field Analysis Comparison Trial (strip trials), is an on-farm experimental testing program employed by Monsanto Company to perform the final evaluation of the commercial potential of a product.

During the next several years, a progressive elimination of hybrids occurs based on more detailed evaluation of their phenotype. Eventually, strip trials (FACT) are conducted to formally compare the experimental hybrids being developed with other hybrids, some of which were previously developed and are commercially successful. That is, comparisons of experimental hybrids are made to competitive hybrids to determine if there was any advantage to further development of the experimental hybrids. After FACT testing is complete, determinations may be made whether commercial development should proceed for a given hybrid.

L. $F_1$ Hybrid Comparisons

As mentioned above, hybrids are progressively eliminated following detailed evaluations of their phenotype, including formal comparisons with other commercially successful hybrids. Strip trials are used to compare the phenotypes of hybrids grown in as many environments as possible. They are performed in many environments to assess overall performance of the new hybrids and to select optimum growing conditions. Because the corn is grown in close proximity, environmental factors that affect gene expression, such as moisture, temperature, sunlight, and pests, are minimized. For a decision to be made to commercialize a hybrid, it is not necessary that the hybrid be better than all other hybrids. Rather, significant improvements must be shown in at least some traits that would create improvements in some niches.

M. Physical Description of $F_1$ Hybrids

The present disclosure provides $F_1$ hybrid corn plants derived from the corn plant CV962284. The physical characteristics of an exemplary hybrid produced using CV962284 as one inbred parent are set forth in Table 2. An explanation of terms used in Table 2 can be found in the Definitions, set forth hereinabove.

TABLE 2

| Morphological Traits for CH010459, a Hybrid Having CV962284 as One Inbred Parent | | |
|---|---|---|
| CHARACTERISTIC | | VALUE |
| 1 | STALK | |
| | Plant Height (cm) | 281.7 |
| | Ear Height (cm) | 114.4 |
| | Anthocyanin | ABSENT |
| | Brace Root Color | ABSENT |
| | Internode Direction | STRAIGHT |
| | Internode Length (cm) | 19.6 |
| 2 | LEAF | |
| | Color | DARK GREEN |
| | Length (cm) | 90.3 |
| | Width (cm) | 10.8 |
| | Sheath Anthocyanin | ABSENT |
| | Sheath Pubescence | HEAVY |
| | Marginal Waves | FEW |
| | Longitudinal Creases | FEW |

TABLE 2-continued

| Morphological Traits for CH010459, a Hybrid Having CV962284 as One Inbred Parent | | |
|---|---|---|
| CHARACTERISTIC | | VALUE |
| 3 | TASSEL | |
| | Length (cm) | 41.6 |
| | Peduncle Length (cm) | 9.1 |
| | Branch Number | 6.4 |
| | Anther Color | SALMON |
| | Glume Color | GREEN & MEDIUM GREEN |
| | Glume Band | ABSENT |
| 4 | EAR | |
| | Silk Color | GREEN - YELLOW |
| | Number Per Stalk | 1 |
| | Position | UPRIGHT |
| | Length (cm) | 18.4 |
| | Shape | CYLINDRICAL |
| | Diameter (mm) | 48.2 |
| | Shank Length (cm) | 8.7 |
| | Husk Bract | SHORT |
| | Husk Cover (cm) | 0.4 |
| | Husk Opening | MODERATE |
| | Husk Color Fresh | GREEN & MEDIUM GREEN |
| | Husk Color Dry | BUFF |
| | Cob Diameter (mm) | 26.9 |
| | Cob Color | RED |
| | Shelling Percent | 90.1 |
| 5 | KERNEL | |
| | Row Number | 16.4 |
| | Number Per Row | 41.8 |
| | Row Direction | STRAIGHT |
| | Type | DENT |
| | Cap Color | YELLOW |
| | Side Color | YELLOW |
| | Length (depth) (mm) | 13.4 |
| | Width (mm) | 8.5 |
| | Thickness (mm) | 4.8 |
| | Endosperm Type | NORMAL |
| | Endosperm Color | YELLOW |

*These are typical values. Values may vary due to environment. Other values that are substantially equivalent are within the scope of the disclosure. Substantially equivalent refers to quantitative traits that when compared do not show statistical differences of their means.

Genetic Complements

The present disclosure provides a genetic complement of the inbred corn plant variety designated CV962284. Further provided by the disclosure is a hybrid genetic complement, wherein the complement is formed by the combination of a haploid genetic complement from CV962284 and another haploid genetic complement. Means for determining such a genetic complement are well known in the art.

As used herein, the phrase "genetic complement" means an aggregate of nucleotide sequences, the expression of which defines the phenotype of a corn plant or a cell or tissue of that plant. By way of example, a corn plant is genotyped to determine a representative sample of the inherited markers it possesses. Markers are alleles at a single locus. They are preferably inherited in codominant fashion so that the presence of both alleles at a diploid locus is readily detectable, and they are free of environmental variation, i.e., their heritability is 1. This genotyping is preferably performed on at least one generation of the descendant plant for which the numerical value of the quantitative trait or traits of interest are also determined. The array of single locus genotypes is expressed as a profile of marker alleles, two at each locus. The marker allelic composition of each locus can be either homozygous or heterozygous. Homozygosity is a condition in which both alleles at a locus are characterized by the same nucleotide sequence or size of a repeated sequence. Heterozygosity refers to different conditions of the gene at a locus. A preferred type of genetic marker for use with the disclosure is simple sequence repeats (SSRs), although potentially any other type of genetic marker could be used, for example, restriction fragment length polymorphisms (RFLPs), amplified fragment length polymorphisms (AFLPs), single nucleotide polymorphisms (SNPs), and isozymes.

A genetic marker profile of an inbred may be predictive of the agronomic traits of a hybrid produced using that inbred. For example, if an inbred of known genetic marker profile and phenotype is crossed with a second inbred of known genetic marker profile and phenotype it is possible to predict the phenotype of the $F_1$ hybrid based on the combined genetic marker profiles of the parent inbreds. Methods for prediction of hybrid performance from genetic marker data is disclosed in U.S. Pat. No. 5,492,547, the disclosure of which is specifically incorporated herein by reference in its entirety. Such predictions may be made using any suitable genetic marker, for example, SSRs, RFLPs, AFLPs, SNPs, or isozymes.

SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise a major part of the methodology. Following amplification, markers can be scored by gel electrophoresis of the amplification products. Scoring of marker genotype is based on the size (number of base pairs) of the amplified segment.

All the compositions and methods disclosed and claimed herein can be made and executed without undue experimentation. While the compositions and methods of this disclosure have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope. More specifically, it will be apparent that certain agents that are both chemically and physiologically related may be substituted for the agents described herein while the same or comparable results would be achieved. All such similar substitutes and modifications apparent to those skilled in the art are deemed to be within the spirit, scope, and concept as defined by the appended claims.

The references cited herein, to the extent that they provide exemplary procedural or other details supplementary to those set forth herein, are specifically incorporated herein by reference.

What is claimed is:

1. A plant of corn variety CV962284, wherein representative seeds of corn variety CV962284 have been deposited under NCMA Accession No. 202306062.

2. A plant part of the plant of claim 1, wherein the plant part comprises a cell of the plant.

3. The plant part of claim 2, further defined as pollen, an ovule, or a cell.

4. A plant part of the plant of claim 1, wherein the plant part comprises a seed of corn variety CV962284.

5. A seed of corn variety CV962284, further comprising a transgene, wherein said transgene was introduced into corn variety CV962284 by backcrossing or genetic transformation, wherein representative seeds of corn variety CV962284 have been deposited under NCMA Accession No. 202306062, and wherein a plant grown from said seed comprises said transgene and otherwise comprises all of the morphological and physiological characteristics of corn variety CV962284 when grown under the same environmental conditions.

6. A composition comprising the seed of claim 4 in plant seed growth media.

7. The composition of claim 6, wherein the plant seed growth media is soil or a synthetic cultivation medium.

8. An $F_1$ hybrid seed produced by crossing the plant according to claim 1 with a second, distinct corn plant.

9. An $F_1$ hybrid seed produced by growing a plant from the seed of claim 5 and crossing said plant with a second, distinct corn plant.

10. An $F_1$ hybrid plant grown from the seed of claim 8.

11. A plant of corn variety CV962284 further comprising a single locus conversion, wherein representative seeds of corn variety CV962284 have been deposited under NCMA Accession No. 202306062, and wherein said plant comprises all the morphological and physiological characteristics of corn variety CV962284.

12. The plant of claim 11, wherein the single locus conversion comprises a transgene.

13. A seed that produces the plant of claim 11.

14. The seed of claim 13, wherein the single locus conversion comprises a nucleic acid sequence that enables site-specific genetic recombination or confers a trait selected from the group consisting of male sterility, herbicide tolerance, insect resistance, pest resistance, disease resistance, modified fatty acid metabolism, abiotic stress resistance, altered seed amino acid composition, and modified carbohydrate metabolism.

15. The seed of claim 14, wherein said single locus conversion that confers herbicide tolerance confers tolerance to benzonitrile herbicides, cyclohexanedione herbicides, imidazolinone herbicides, phenoxy herbicides, sulfonylurea herbicides, triazine herbicides, 1-aminocyclopropane-1-carboxylic acid synthase-inhibiting herbicides, 4-hydroxyphenylpyruvate dioxygenase-inhibiting herbicides, acetolactate synthase-inhibiting herbicides, protoporphyrinogen oxidase-inhibiting herbicides, 2,4-dichlorophenoxyacetic acid, bromoxynil, dicamba, glufosinate, glyphosate, nicosulfuron, or quizalofop-p-ethyl.

16. A method of producing a progeny corn plant derived from corn variety CV962284, said method comprising applying plant breeding techniques to the plant of claim 1 or an $F_1$ hybrid thereof to yield said progeny corn plant.

17. The method of claim 16, wherein said plant breeding techniques comprise backcrossing, marker assisted breeding, genomic selection, pedigree breeding, selfing, outcrossing, haploid production, doubled haploid production, or transformation.

18. The method of claim 16, further defined as comprising:

(a) selfing the plant of corn variety CV962284 or an $F_1$ hybrid thereof or crossing said plant of corn variety CV962284 or said $F_1$ hybrid thereof with a different plant, to produce a seed of a progeny plant of a subsequent generation;

(b) growing a progeny plant of a subsequent generation from the seed of the progeny plant of a subsequent generation; and (c) repeating steps (a) and (b) with sufficient inbreeding to produce an inbred corn plant derived from corn variety CV962284.

19. A method of producing a commodity plant product, said method comprising producing the commodity plant product from the plant of claim 10.

20. The method of claim 19, wherein said commodity plant product is grain, starch, seed oil, corn syrup, or protein.

\* \* \* \* \*